(12) United States Patent
Demin et al.

(10) Patent No.: US 8,247,407 B2
(45) Date of Patent: Aug. 21, 2012

(54) PHARMACEUTICAL COMPOSITION WITH ANTI-DIABETIC ACTION

(75) Inventors: Alexander Victorovich Demin, Moscow (RU); Vitaly Afanasievich Martianov, Moscow (RU); Alexander Mihaylovich Shuster, Moscow (RU)

(73) Assignee: Zakrytoe Artsionernoe Obschestvo "Masterclone", Moscow (RU)

( * ) Notice: Subject to any disclaimer, the term of this patent is extended or adjusted under 35 U.S.C. 154(b) by 108 days.

(21) Appl. No.: 12/673,243

(22) PCT Filed: May 22, 2008

(86) PCT No.: PCT/RU2008/000320
§ 371 (c)(1),
(2), (4) Date: Feb. 12, 2010

(87) PCT Pub. No.: WO2009/035368
PCT Pub. Date: Mar. 19, 2009

(65) Prior Publication Data
US 2010/0168092 A1 Jul. 1, 2010

(30) Foreign Application Priority Data
Sep. 14, 2007 (RU) .................. 2007134267

(51) Int. Cl.
*A61K 31/5365* (2006.01)
*A61K 31/403* (2006.01)
*A61K 31/4439* (2006.01)
*A61K 31/5377* (2006.01)
*A61K 31/497* (2006.01)
*A61P 7/12* (2006.01)

(52) U.S. Cl. ............ 514/229.8; 514/419; 514/339; 514/235.2; 514/254.09

(58) Field of Classification Search ............ None
See application file for complete search history.

(56) References Cited

U.S. PATENT DOCUMENTS
5,219,859 A 6/1993 Festal et al.
2005/0277685 A1 12/2005 Acton, III et al.
2009/0326037 A1 12/2009 Leneva

FOREIGN PATENT DOCUMENTS

| | | | |
|---|---|---|---|
| EP | 2 036 889 A2 | 3/2009 |
| RU | 2 074 179 C1 | 2/1997 |
| RU | 2 328 483 C2 | 7/2008 |
| RU | EP 2 036 889 A2 * | 3/2009 |
| WO | WO 2004/020409 | 11/2004 |
| WO | WO 2005/102320 A1 | 11/2005 |
| WO | WO 2007/075102 A1 | 7/2007 |
| WO | WO 2007/136300 A2 | 11/2007 |
| WO | WO 2007/136302 A2 | 11/2007 |
| WO | WO 2007/136302 A2 | 11/2007 |
| WO | WO 2008/100977 * | 8/2008 |
| WO | WO 2009/016526 A2 | 2/2009 |
| WO | WO 2009/035368 A1 | 3/2009 |

OTHER PUBLICATIONS

Anisimova et al. in the Pharmaceutical Chemistry Journal, vol. 29, No. 2, pp. 78-82 (1995).*
50 Ways to PRevent Diabetes in http://ndep.nih.gov/media/50Ways_tips.pdf downloaded Dec. 2, 2011.*
Can Diabetes be Prevented? www.joslin.org/info/can_diabetes_be_prevented.html (downloaded Dec. 2, 2011).*
Type-1 diabetes (www.mayoclinic. com/health /type -1-diabetes/DS00329/DSECTION=treatments-and-drugs) (downloaded Dec. 4, 2011).*
Anisimova, O.S., "Study of Metabolism of the Antiviral Drug Arbidol by Mass Spectometry, Thin-Layer and High Performance Liquid Chromotography" Pharmaceutical Chemistry Journal vol. 29, No. 2, 1995, pp. 78-82.
International Search Report for PCT/RU 2008/000320 mailed on Nov. 13 2008.
Zotova, S.A., "Synthesis and Antiviral Activity of Indole and Benzofuran Sulfides" Pharmaceutical Chemistry Journal, vol. 29, No. 1, 1995, pp. 57-59.
English Abstract of WO2007/136302.
English Abstract of WO/2005/102320.

* cited by examiner

*Primary Examiner* — Timothy Thomas
*Assistant Examiner* — Dennis Heyer
(74) *Attorney, Agent, or Firm* — Woodard, Emhardt, Moriarty, McNett & Henry LLP

(57) ABSTRACT

The invention relates to medicine, in particular to searching and developing novel medicinal agent for treating pancreatic diabetes. The invention is based on the development of more effective and less toxic medicinal agents based on indole derivatives which exhibit antidiabetic, hypolipidemic, hypoglycemic, hypocholesterolemic activity and insulin resistance-improving actions and the structure of which differs from the structure of traditionally used compounds. The inventive indole derivatives are also low-toxic and easily tolerated.

10 Claims, 2 Drawing Sheets

PHARMACEUTICAL COMPOSITION WITH ANTI-DIABETIC ACTION

REFERENCE TO RELATED APPLICATIONS

This application is a National Stage of International Application PCT/RU2008/000320 filed May 22, 2008, which was published in Russian. Applicant claims foreign priority benefits under 35 U.S.C. 119(a)-(d) of the following foreign application for patent: Russian Application No. RU2007/134267, filed Sep. 14, 2007, which is incorporated herein by reference.

FIELD OF INVENTION

The invention relates to pharmaceutical compositions with anti-diabetic, hypocholesteremic, hypolipidemic and hypoglycemic action suitable for preparation of medicinal drugs in the form of tablets, granules, capsules, suspensions, solutions or injections.

PRIOR ART

Diabetes mellitus is a disease that is manifested by high blood glucose level due to the insufficient effect of insulin. Insulin is the hormone that is produced by the pancreas, in particular, by the beta-cells of Langerhans islets. During diabetes mellitus, insulin is either virtually absent (type I diabetes, or insulin-dependent diabetes), or the body cells insufficiently react to insulin (type II diabetes, or insulin-independent diabetes). Due to the insufficient insulin effect, the following events take place: blood glucose increases (hyperglycemia), glucose is excreted with urine (glucosuria), and blood accumulates the acidic products of abnormal fat burning known as ketone bodies (ketoacidosis). Treatment depends on the type of diabetes. Type I diabetes is treated with insulin only, which compensates for the absence of natural insulin in the body. For treatment of type II diabetes, the anti-diabetic oral drugs are mainly used.

With every passing year, the number of diabetic patients in the world is growing. This process is facilitated by such factors as the global population growth, population "aging", urbanization, expansion of obesity, low physical activity, etc. According to the experts' forecast, the prevalence of diabetes mellitus in all age groups will rise by 2030 from 2.8% in 2000 to 4.4%, with the highest rate among the urban citizens of developing countries. In absolute figures, by 2030, the total number of diabetes patients will grow from current 171 million to 366 million people. In this regard, the most important thing seems to be the search for new medicinal drugs with strong anti-diabetic action reducing blood glucose level and having the hypocholesteremic and hypolipidemic effect.

Currently, two types of medicinal drugs are used for diabetes treatment: insulin or its substitutes and oral anti-diabetic drugs. The latter are divided into several main groups: derivatives of sulphonylurea, biguanides, and inhibitors of 10 alpha-glucosidases. Sulphonylurea derivatives mainly stimulate pancreatic islets' beta-cells which are accompanied by mobilization and enhanced output of endogenous insulin. The presence of functionally active beta-cells in the pancreas is a prerequisite for the effect of anti-diabetic drugs. It is believed that these drugs "close" the beta-cells' potassium channels, reduce potassium egress in the extracellular space and stimulate the insulin release. Besides, the derivatives of sulphonylurea increase the number of insulin-sensitive receptors on the target cells. However, the long-term administration of sulphonylurea drugs brings about the exhaustion of pancreatic 2-cells' function which is accompanied by decline in the diabetes mellitus compensation and significant hyperglycemia which, in turn, aggravates the existing insulin resistance (secondary insulin resistance) in case of the type 2 diabetes mellitus. Treatment by derivatives of sulphonylurea is contraindicated during diabetes mellitus type 1 or secondary (pancreatic) diabetes mellitus, pregnancy and breastfeeding (because of their teratogenic effect), surgical interventions (major operations), severe infections, injuries, and risk of severe hypoglycemias.

The effect of biguanides is mainly confined to suppression of glyconeogenesis in the liver (inclusive of glycogenolysis) and augmentation of peripheral utilisation of glucose. They also restrain the inactivation of insulin. Biguanides affect the carbohydrate metabolism in the liver and muscles, increase glucose utilisation without oxygen access (anaerobic glycolysis) and, thereby, may bring about the increased level of lactic acid and lactacidosis, primarily in patients with cardiac failure, for whom these compounds are not recommended.

The inhibitors of alpha-glycosidase restrain cleavage of poly- and oligosaccharides, thus reducing the formation and intestinal absorption of glucose and thereby preventing the development of post-prandial hyperglycemia. However, their administration may cause the development of dyspepsia. As a result, about 60% of patients are constrained to stop taking drugs within the first three years of drug administration.

Recently, the new groups of oral anti-diabetic medicinal drugs have appeared. The phenyl alanine derivatives act by enhancing tissue sensitivity to endogenous insulin, which is why they are also called the insulin secretogens. The carbamoylbenzoic acids block the ATP-dependent potassium channels in the membranes of functionally active beta-cells in the pancreatic isles, induce their de-polarization and the opening of calcium channels, and thereby induce insulin secretion.

The most promising medicinal drugs are thiazolidinodiones (or glitazones) which modulate transcription of the insulin-sensitive genes and participate in the glucose level control and lipid metabolism in the fat and muscle tissues, as well as in the liver. Therefore, the glitazones restore patient's sensitivity to his own insulin. The blood glucose and triglyceride content returns to normal, which eliminates, or at least lowers the need for the exogenous insulin. The glitazones are fairly well tolerated and do not cause hypoglycemia. However, the glitazones administration provokes a weight gain which in itself complicates the course of diabetes. Besides, the recent data have demonstrated that in patients who took Avandia (related to glitazones), the probability of myocardial infarction was 43% higher, and the fatality rate after infarction was 64% higher in the Avandia group as compared to the untreated group (New England Journal of Medicine, v. 356: 2457-2471).

Assuming the abovementioned, the search for new anti-diabetic drugs remains current.

At present, apart from the already known classes of compounds, such as derivatives of sulphonylurea or phenyl alanine, biguanides and thiazolidinodiones, there is a large number of compounds with anti-diabetic action. For instance, there are the derivatives of substituted phenylpropionic acid (RU patent No. 2 300 517 and RU patent No. 2 303 031), derivatives of hexahydrodiazepinone (RU patent No. 2 301 803), and derivatives of oxazolarylpropionic acids (RU patent No. 2 303 593), etc.

However, as many of the listed compounds with anti-diabetic action are yet to pass the clinical trials and, hence, can only potentially be considered as medicinal drugs, we have chosen, as the closest analogue, the metformin (biguanid) having proven anti-diabetic action. For instance, the "Desktop manual for diabetes mellitus type 2", published by the International Diabetes Federation (IDF) in 1999, nominates metformin as number one on the list of glucose-lowering drugs recommended for oral administration

DISCLOSURE OF THE INVENTION

The technical result of the present invention is the creation of a novel pharmaceutical composition on the basis of indole derivatives with anti-diabetic, hypocholesteremic, and hypoglycemic action, reducing the blood lipid level and improving insulin-resistance, and having a structure that is different from the traditionally used compounds. This will allow to extend the number of anti-diabetic drugs. The indole derivatives proposed in this invention possess, apart from their anti-diabetic effect, low toxicity and good tolerability.

The indicated result is achieved by creation of the pharmaceutical composition with the anti-diabetic, hypolipidemic, hypocholesteremic and hypoglycemic action for preparation of medicinal drugs in the form of tablets, granules, capsules, suspensions, solutions, or injections containing, as an active substance, the compounds derived from the common formula (I):

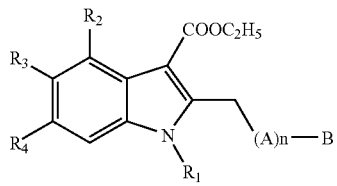

where:
$R_1$ is chosen from the eventually substituted alkyl, oxyalkyl, or cycloalkyl, eventually substituted heterocyclil or eventually substituted aryl. As the substituents, there are the lowest alkyl, halogen, oxyalkyl, hydroxyl group, amino group or several of the listed substituents at the same time.
$R_2$—H, —$CH_2N(R'R'')_2$; where R' and R'', independently of each other, is the substituent of amino group, chosen from hydrogen, eventually substituted alkene, alkyl or cycloalkyl, alkoxy group, eventually substituted heterocyclil, eventually substituted aryl, or R' and R'', along with the nitrogen atom with which they are bound, form guanidyl or eventually substituted azaheterocyclil.
$R_3$ is an alkoxy group, or OH, or $R_2$ and $R_3$ form together the eventually substituted oxazine cycle;
$R_4$ is chosen from hydrogen, halogen, cyano group, $NO_2$-group, trifluoromethyl, eventually substituted aryl or eventually substituted heterocyclil;
A—S, SO, $SO_2$ B—$(CH_2)_k$—$R_5$, where $R_5$ is the eventually substituted aryl, eventually substituted alkyl or oxyalkyl, eventually substituted heterocyclil,
or $R_5$ is the substituent of the type:

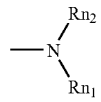

where $Rn_1$ and $Rn_2$ are defined also as the substituents R' and R'';
n=0-1; k=0-2,
or hydrates and/or pharmaceutically acceptable salts of the compound in formula I, as well as pharmaceutically acceptable carrier and/or excipient.

The mentioned compounds corresponding to formula I, inclusive of their synthesis and physico-chemical properties, are described in the literature (Khimiko-Farmatsevticheskii Zhurnal, No. 2I, 1995, p. 51-53, Khimiko-Farmatsevticheskii Zhurnal, JSTs 2; 1995, p. 5-8; Khimiko-Farmatsevticheskii Zhurnal, No. 5, 1988, p. 565-569), as well as in the international application PCT/RU2007/000246. All final chemical compounds in the invention have been obtained using the methods described in the above literature, or can be obtained using the analogous methods, as those are known to the expert in the field of organic chemistry. However, until now, it was not known that the compounds corresponding to formula I exhibit the anti-diabetic action, which was shown by the authors of the invention for the first time. In the most general variant, the invention discloses the pharmaceutical compositions which contain, as an active component, the effective quantity of the compound of general formula I.

The mentioned chemical compounds may have asymmetric centers and, therefore, they can exist as different enantiomers and diastereomers. This invention also deals with pharmaceutical compositions which contain optical isomers, racemates of compounds of formula I, as well as their mixtures. The "racemates" imply the mixtures containing equal quantities of enantiomer pairs.

Besides, the invention also includes the pharmaceutical compositions which contain pro-drugs. According to the invention, the pro-drugs are derivatives of chemical compounds of general formula I which, by itself, may have a relatively weak or no action. However, after drug intake in physiological conditions (for instance, in the course of its metabolism, due to its solvolysis, or by some other mechanism), they can be converted into the biologically active forms.

The following compounds are most preferable for use as the active components (the chemical formulas and brief descriptions are given in Table 1, and for the convenience of their description further in the text and in the formula of invention).

TABLE 1

Formulas, names and designations of compounds according to the invention.

| Formula of compound | Designation | Chemical name |
|---|---|---|
| (structure shown) *HCl*$H_2O$ | MC-200 | 1-methyl-2-phenylthiomethyl-3-carbethoxy-4-dimethylaminomethyl-5-hydroxy-6-bromoindole hydrochloride |

TABLE 1-continued

Formulas, names and designations of compounds according to the invention.

| Formula of compound | Designation | Chemical name |
|---|---|---|
| | MC-201 | 1-methyl-2-p-toluilthiomethyl-3-carbethoxy-4-dimethyl-aminomethyl-5-hydroxy-6-bromoindole |
| | MC-202 | 1-methyl-2-(p-ethyl)-phenyl-thiomethyl-3-carbethoxy-4-dimethylaminomethyl-5-hydroxy-6-bromoindole |
| | MC-203 | 1-methyl-2-(p-ethoxy)-phenylthiomethyl-3-carbethoxy-4-dimethylaminomethyl-5-hydroxy-6-bromoindole |
| | MC-204 | 1-p-toluyl-2-phenylthiomethyl-3-carbethoxy-4-dimethylaminomethyl-5-hydroxy-6-bromoindole |
| | MC-205 | 1-benzyl-2-phenylthiomethyl-3-carbethoxy-4-dimethylaminomethyl-5-hydroxy-6-bromoindole |

TABLE 1-continued

Formulas, names and designations of compounds according to the invention.

| Formula of compound | Designation | Chemical name |
|---|---|---|
| | MC-206 | 1-methyl-2-benzylthiomethyl-3-carbethoxy-4-dimethylaminomethyl-5-hydroxy-6-bromoindole |
| | MC-207 | 1-methyl-2-pyrrolidinyl-1-methyl-3-carbethoxy-5-hydroxy-6-(pyridine-3-yl)indole |
| | MC-208 | 1-methyl-2-dimethylaminomethyl-3-carbethoxy-5-hydroxy-6-(pyridine-3-yl)indole |
| | MC-209 | 8-dimethylaminomethyl-9-carbethoxy-2,7-dimethyl-5-pyridine-3-yl-1,2,3,7-tetrahydro[1,3]oxazino[5,6-e]indole |
| | MC-210 | 1-methyl-2-phenylsulfonylmethyl-3-carbethoxy-4-dimethylaminomethyl-5-hydroxy-6-(pyridine-3-yl)indole |
| | MC-211 | 1-methyl-2-dimethylaminomethyl-3-carbethoxy-4-pyrrolidinomethyl-5-hydroxy-6-(pyridine-3-yl)indole trihydrochloride |

*3HCl

TABLE 1-continued

Formulas, names and designations of compounds according to the invention.

| Formula of compound | Designation | Chemical name |
|---|---|---|
| | MC-212 | 1-methyl-2-pyrrolidinomethyl-3-carbethoxy-4-dimethylaminomethyl-5-hydroxy-6-(pyridine-3-yl)indole trihydrochloride |
| | MC-213 | 9-carbethoxy-2,7-dimethyl-5-pyridine-3-yl-8-[(pyrrolidine-1-yl)methyl]-1,2,3,7-tetrahydro[1,3]oxazino[5,6-e] indole trihydrochloride |
| | MC-214 | 1-methyl-2-phenylsulfonylmethyl-3-carbethoxy-4-methylaminomethyl-5-hydroxy-6-pyridinyl-3 indole dihydrochloride |
| | MC-215 | 1-methyl-2-phenylthiomethyl-3-carbethoxy-4-dimethylaminomethyl-5-hydroxy-6-pyridinyl-3 indole |
| | MC-216 | 1-methyl-2-phenylthiomethyl-3-carbethoxy-4-dimethylaminomethyl-5-hydroxy-6-cyano indole |
| | MC-217 | 1-methyl-2-β-naphthylthiomethyl-3-carbethoxy-4-dimethylaminomethyl-5-hydroxy-6-bromoindole hydrochloride |

*HCl*H$_2$O

TABLE 1-continued

Formulas, names and designations of compounds according to the invention.

| Formula of compound | Designation | Chemical name |
|---|---|---|
| 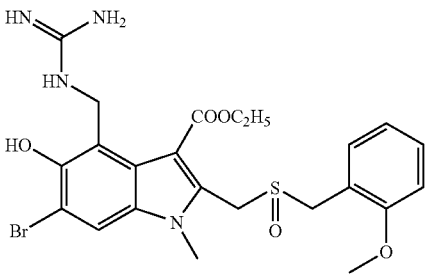 *HCl | MC-218 | 1-methyl-2-(o-methoxy)-benzylsulfinylmethyl-3-carbethoxy-4-guanidinomethyl-5-hydroxy-6-bromoindole hydrochloride |
| 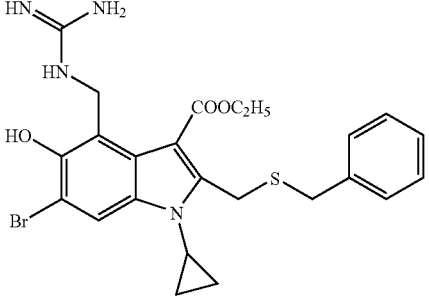 | MC-219 | 1-cyclopropyl-2-benzylthiomethyl-3-carbethoxy-4-guanidinomethyl-5-hydroxy-6-bromoindole |
| 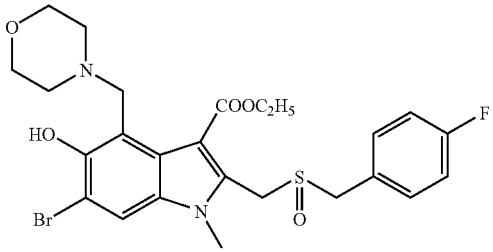 *HCl | MC-220 | 1-methyl-2-(p-fluor)-benzylsulfinylmethyl-3-carbethoxy-4--4-morpholinomethyl-5-hydroxy-6-bromoindole hydrochloride |
| 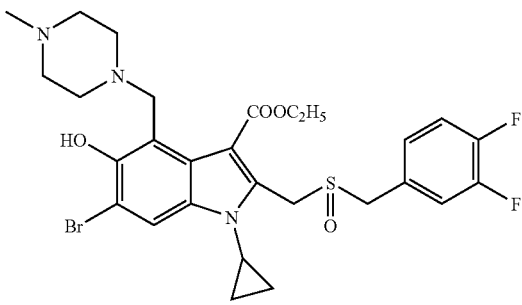 *2HCl | MC-221 | 1-cyclopropyl-2-(3,4-difluor)benzylsulfinyl-methyl-3-carbethoxy-4-(N-methyl)-piperazinomethyl-5-hydroxy-6-bromoindole dihydrochloride |
| 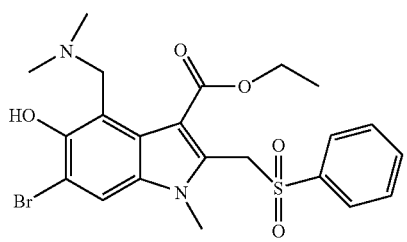 | MC-222 | 1-methyl-2-phenylsulfonylmethyl-3-carbethoxy-4-dimethylaminomethyl-5-hydroxy-6-bromoindole |

TABLE 1-continued

Formulas, names and designations of compounds according to the invention.

| Formula of compound | Designation | Chemical name |
|---|---|---|
|  | MC-223 | 1-methyl-2-phenylsulfinylmethyl-3-carbethoxy-4-dimethylaminomethyl-5-hydroxy-6-bromoindole |
|  | MC-224 | 1-methyl-2-phenylsulfonylmethyl-3-carbethoxy-5-hydroxy-6-bromoindole |
|  | MC-225 | 1-methyl-2-phenylsulfinylmethyl-3-carbethoxy-5-hydroxy-6-bromoindole |

The compounds of formula (I), according to the invention, can be used as active components of the pharmaceutical compositions for treatment of non-insulin-dependent diabetes mellitus.

The particular feature of pharmaceutical composition is that, as an active substance, the compound of formula I or its pharmaceutically acceptable salts and/or hydrates can be used. To produce the pharmaceutical composition, it is preferable to mix the active substance with the excipients inert to the substance, with the following preparation of tablets, granules, capsules, suspensions, dissolving or diluting, and placing them in suitable packaging.

In patients, the dosage of pharmaceutical composition containing the compound of formula I as an active ingredient can be corrected depending on the therapeutic efficiency and bioavailability of active ingredients in the body, rate of their metabolism and excretion from the body. Besides, the effective dose can also depend on the patient's weight, age and gender, and the presence of concomitant diseases. The daily dose in adults can be 10-1,000 mg, preferably 50-250 mg. In accordance with physician's directions, this drug can be taken several times a day, for instance, from one to five times, preferably from one to three times.

Below, there are several terms that have been used for the description of this invention.

The term "alkyl" refers to the saturated aliphatic hydrocarbonic residue with linear or branched chain containing from one to twenty carbon atoms, preferably from one to fifteen carbon atoms, even more preferably from one to five carbon atoms.

The term "oxyalkyl" refers to the RO— group, in which the R represents alkyl. It is preferable (but not limited to the listed variants) to use the following oxyalkyls: methoxy, ethoxy, propoxy, isopropoxy, butoxy or isobutoxy.

The term "lower alkyl" or "lower oxyalkyl" is used for designation of the group in which the carbon part contains from one to seven, preferably from one to four, carbon atoms.

The term "aryl" designates the aromatic system, mono- or polycyclic, which includes from 6 to 14 carbon atoms, mainly from 6 to 10 carbon atoms. The aryl may contain one or more substituents which can be same or different. The preferred variants are optionally substituted phenyl, and optionally substituted naphthyl.

The term "substituted phenyl" refers to the phenyl group, preferably mono- or polysubstituted, for instance, mono-, di- or trisubstituted by halogen, hydroxyl, lower alkyl or cycloalkyl, lower oxyalkyl, amino group, hydroxy group, etc., the preferable substituents being halogen, lower alkyl and/or lower oxyalkyl.

The term "substituted naphthyl" refers to the naphthyl group, preferably containing (but not limited to them) such substituents as halogen, lower alkyl and/or lower alkoxy.

The term "heterocyclil" means the aromatic (heteroaryl) or non-aromatic (alkyl or alken) cyclic system which can be either mono- or polycyclic including 3 to 14 carbon atoms, mainly 5 to 6 carbon atoms, in which one or several carbon atoms are substituted for a hetero atom such as nitrogen, oxygen or sulfur, which may be emphasized by addition of corresponding prefix "aza", "oxa" or "thia" before heterocyclil. The heterocyclil may contain one or several substituents which could be either same or different. The preferable heterocyclils are morpholin, piperazin, piperidin, pirrolidin, thyazolidin, tetrahydrofuran, etc.

The term "heteroaryl" means the aromatic monocyclic or polycyclic system which includes 5 to 14 carbon atoms, preferably 5 to 10, in which one or more carbon atoms are substituted for hetero atom or hetero atoms, such as nitrogen, oxygen or sulfur. The heteroaryl may have one or several substituents which could be either same or different. The preferable heteroaryls are furanyl, thenyl, pyridyl, pyrazinyl, pyrimidinyl, thiazolyl, pyrazolyl, furazanyl or triazolyl.

The term "pharmaceutically acceptable salt" means the adequately non-toxic organic and inorganic salts of acids and alkali typically used for this purpose. For instance, such salts can be obtained based on a free base of the claimed compound and the appropriate organic or inorganic acid. The most preferable salt variants are hydrochlorides, hydrobromides, sulfates, bi-sulfates, phosphates, nitrates, acetates, mesilates, tosilates, citrates, benzolsulphonates, etc. (more detailed description of such salts' properties can be found in "Pharmaceutical Salts", J. Pharm. Sci. 1977, 66: 1-19.). The term "pharmaceutically acceptable salts" also includes the pharmaceutically acceptable solvates, preferably hydrates.

The term "pharmaceutical composition" means the composition that includes the compound of formula I and at least one of the components that have been chosen from the group comprising the pharmaceutically acceptable and pharmaceutically compatible carriers, fillers, excipients, solvents or diluents, delivery vehicles, preservation agents, stabilizers and other target additives as indicated, for instance, in the "Handbook of Pharmaceutical Excipients" ($2_{nd}$ ed. London: The Pharmaceutical Press; 1994). Along with the excipients, it is possible to use humidifiers, emulsifiers, thickening agents, sweeteners, flavorings, aromatizers, regulators of prolonged delivery (for instance, aluminum monostearate and gelatin), suspending agents (for instance, ethoxylated isostearyl alcohol, polyoxyethylenesorbitol and sorbitic ether, microcrystalline cellulose, aluminum metahydroxide, bentonite, as well as the mixtures of these substances); such fillers as lactose, milk sugar, sodium citrate, calcium carbonate, calcium phosphate; such blenders as starch, alginic acid and its salts, silicates; antibacterial and antifungal agents (for instance, parabens, chlorobutanol, sorbic acid).

The compositions intended for injections can also incorporate isotonic agents, for instance, sugar, sodium chloride, etc. The following can be used as suitable carriers, solvents, diluents, and delivery vehicles: water, ethanol, various polyalcohols, as well as water-alcohol, plant oils and injection organic complex ethers (for instance, ethyl oleate).

The indicated excipients can be used in combination with other active ingredients provided they do not cause adverse effects, for instance, allergic reactions.

The pharmaceutical composition can be used for oral, sublingual, intramuscular, intravenous, subcutaneous, topical, or rectal administration. The suitable standard dosage forms include tablets, capsules, pills, powders, granules, chewing gums, solutions or suspensions, aerosols, implants, drops, suppositories, and ointments.

The invention is illustrated by, but is not confined to the following examples.

EXAMPLE 1

Hypoglycemic Drug Activity

The blood glucose changes are the main indicator of efficiency of diabetes treatment. That is why the given parameter allows to evaluate the drug group action and select the most promising compounds for further work.

The pharmaceutical compositions for determination of anti-diabetic action had the following composition: active compound—1 g, potato starch—1 g, water—100 ml.

The comparison of anti-diabetic action of compounds was carried out using a standard model of alloxan diabetes and metmorphin as a comparative drug. The alloxan diabetes was induced by a single subcutaneous injection of water solution of alloxan hydrate (ICN Biomedicals, USA) at a dose of 150 mg/kg to rats weighting 180-200 g that have fasted for 24 hours. The following animal groups were studied: intact rats, diabetic non-treated rats, diabetic rats receiving Polfa-Kutno Ltd." metmorphin daily (for 23 days, 200 mg/kg); diabetic rats receiving daily (for 20 days) the abovementioned pharmaceutical compositions containing, as an active components, the compounds described in this invention: MC-200-MC-225. The compounds were administered intragastrically once a day in starch gel at a dose of 50 mg/kg rat weight.

The experimental drug doses were selected assuming the expected therapeutic doses for man and previously determined toxic doses ($LD_{50}$ of studied compounds was approximately 500-1,000 mg/kg). The metmorphin dose for rats was extrapolated from the therapeutic dose for man. Drug administration was started on the third day after alloxan injection when blood glucose level increased approximately 3-fold as compared to control value. Each group consisted of 20 animals of both genders. The results obtained are presented in Table 2.

TABLE 2

Results of glucose level determination in diabetic rats' blood.

| Compound code | Glucose content, mmol/l, in 10 days | Glucose content, mmol/l, in 20 days |
|---|---|---|
| MC-200 | 5.6 ± 0.2 | 5.4 ± 0.3 |
| MC-201 | 6.4 ± 0.4 | 6.2 ± 0.3 |
| MC-202 | 7.3 ± 0.5 | 7.0 ± 0.4 |
| MC-203 | 6.3 ± 0.2 | 6.1 ± 0.3 |
| MC-204 | 6.4 ± 0.3 | 6.2 ± 0.3 |
| MC-205 | 8.4 ± 0.6 | 8.1 ± 0.5 |
| MC-206 | 11.2 ± 0.7 | 10.8 ± 0.6 |
| MC-207 | 5.5 ± 0.2 | 5.0 ± 0.3 |
| MC-208 | 9.8 ± 0.4 | 9.5 ± 0.4 |
| MC-209 | 5.6 ± 0.3 | 5.4 ± 0.5 |
| MC-210 | 5.4 ± 0.2 | 5.3 ± 0.3 |
| MC-211 | 5.0 ± 0.2 | 4.8 ± 0.2 |
| MC-212 | 5.2 ± 0.3 | 5.1 ± 0.3 |
| MC-213 | 5.8 ± 0.4 | 5.5 ± 0.3 |
| MC-214 | 10.2 ± 0.8 | 9.9 ± 0.7 |
| MC-215 | 5.6 ± 0.2 | 5.4 ± 0.3 |
| MC-216 | 8.4 ± 0.4 | 8.1 ± 0.4 |
| MC-217 | 5.2 ± 0.2 | 4.8 ± 0.3 |
| MC-218 | 7.2 ± 0.4 | 7.1 ± 0.4 |
| MC-219 | 9.3 ± 0.6 | 9.0 ± 0.5 |
| MC-220 | 5.9 ± 0.2 | 5.8 ± 0.2 |
| MC-221 | 7.3 ± 0.4 | 7.2 ± 0.4 |
| MC-222 | 6.4 ± 0.3 | 6.2 ± 0.3 |
| MC-223 | 8.4 ± 0.6 | 8.2 ± 0.6 |
| MC-224 | 6.5 ± 0.4 | 6.3 ± 0.3 |
| MC-225 | 8.2 ± 0.5 | 7.9 ± 0.4 |
| Metmorphin | 6.6 ± 0.3 | 6.4 ± 0.3 |
| Intact rats | 4.5 ± 0.2 | 4.2 ± 0.2 |
| Non-treated diabetic rats | 16.2 ± 0.6 | 18.6 ± 1.2 |

Based on the data obtained, we selected several active compounds for more detailed analysis.

EXAMPLE 2

Anti-Diabetic, Hypolipidemic and Hypocholesteremic Activity of Pharmaceutical Compositions Containing, as Active Substances, One of the Compounds of General Formula I Pharmaceutical compositions for determination of anti-diabetic action had the same composition as that given in Example I.

The comparison of the anti-diabetic action of compounds was carried out using a standard model of alloxan diabetes, as described in Example I, and metmorphin as a comparative drug.

In the course of experiment, the following parameters were recorded: animal general condition, water consumption, body mass, levels of glucose, total lipids, tri-glycerides, serum blood cholesterol, and glycosylated hemoglobin, using the generally accepted techniques (Laboratory methods of studies in clinical practice, V. V. Menshikov, Ed., Moscow, "Medicine", 1987). The integral values of carbohydrate and lipid metabolism in white rats with experimental diabetes are presented in Tables 3, 4, 5, and 6.

TABLE 3

| Values | Intact | Diabetes | Diabetes + metmorphin | Diabetes + MC-217 | Diabetes + MC-200 |
|---|---|---|---|---|---|
| In 10 days | | | | | |
| Percent of survived rats | 100 | 70 | 100 | 100 | 100 |
| Body mass, g | 180 ± 5 | 185 ± 10 | 185 ± 5 | 190 ± 10 | 180 ± 5 |
| Daily water consumption, ml | 15 ± 1 | 45 ± 2 | 25 ± 3* | 25 ± 5* | 20 ± 3* |
| Glucose, mmol/l | 4.5 ± 0.3 | 16.2 ± 0.5 | 6.6 ± 0.3* | 5.2 ± 0.2* | 5.6 ± 0.2* |
| In 20 days | | | | | |
| Percent of survived rats | 100 | 50 | 80 | 100 | 75 |
| Body mass, g | 195 ± 10 | 165 ± 10 | 180 ± 5 | 185 ± 10 | 182 ± 10 |
| Daily water consumption, ml | 17 ± 2 | 55 ± 2 | 20 ± 3* | 22 ± 5* | 24 ± 6* |
| Glucose, mmol/l | 4.2 ± 0.2 | 18.6 ± 1.2 | 6.4 ± 0.2* | 4.8 ± 0.1* | 5.4 ± 0.3* |

TABLE 4

| Values | Intact | Diabetes | Diabetes + metmorphin | Diabetes + MC-217 | Diabetes + MC-200 |
|---|---|---|---|---|---|
| In 10 days | | | | | |
| Cholesterol, mmol/l | 1.4 ± 0.3 | 7.2 ± 0.2 | 2.6 ± 0.3* | 2.4 ± 0.2* | 2.7 ± 0.4* |
| Total lipids, g/l | 10.2 ± 0.3 | 17.4 ± 1.2 | 10.6 ± 0.6* | 10.4 ± 0.5* | 10.2 ± 0.5* |
| Tri-glycerides, mmol/l | 2.5 ± 0.2 | 2.8 ± 0.4 | 2.6 ± 0.1 | 2.3 ± 0.2 | 2.5 ± 0.2 |
| β-lipoproteins, g/l | 2.0 ± 0.3 | 4.5 ± 0.1 | 2.2 ± 0.3* | 2.1 ± 0.2* | 2.0 ± 0.2* |
| Glycosylated hemoglobin, mol % | 4.5 ± 0.5 | 8.4 ± 0.2 | 5.1 ± 0.1* | 5.2 ± 0.2* | 6.2 ± 0.3* |
| In 20 days | | | | | |
| Cholesterol, mmol/l | 1.2 ± 0.2 | 7.6 ± 0.3 | 1.7 ± 0.3* | 1.4 ± 0.2* | 1.5 ± 0.2* |
| Total lipids, g/l | 10.1 ± 0.3 | 18.5 ± 1.3 | 11.6 ± 1.2* | 10.2 ± 0.3* | 10.6 ± 1.0* |
| Tri-glycerides, mmol/l | 2.5 ± 0.2 | 2.9 ± 0.4 | 1.6 ± 0.1 | 1.5 ± 0.2 | 1.5 ± 0.2 |
| β-lipoproteins, g/l | 2.0 ± 0.3 | 4.5 ± 0.2 | 2.2 ± 0.3* | 2.1 ± 0.2* | 2.1 ± 0.3* |
| Glycosylated hemoglobin, mol % | 4.5 ± 0.5 | 12.5 ± 0.3 | 6.2 ± 0.2* | 4.9 ± 0.3* | 6.5 ± 05* |

*significant difference from the non-treated animal group ($p < 0.05$).

TABLE 5

| Values | Intact | Diabetes | Diabetes + metmorphin | Diabetes + MC-207 | Diabetes + MC-213 |
|---|---|---|---|---|---|
| In 10 days | | | | | |
| Percent of survived rats | 100 | 70 | 100 | 100 | 90 |
| Body mass, g | 181 ± 5 | 185 ± 10 | 185 ± 5 | 186 ± 10 | 185 ± 5 |
| Daily water consumption, ml | 15 ± 1 | 45 ± 2 | 25 ± 3 | 24 ± 5* | 26 ± 5* |
| Glucose, mmol/l | 4.3 ± 0.3 | 16.5 ± 0.5 | 6.4 ± 0.3* | 5.5 ± 0.3 | 5.8 ± 0.3* |
| In 20 days | | | | | |
| Percent of survived rats | 100 | 50 | 80 | 90 | 75 |
| Body mass, g | 196 ± 9 | 168 ± 10 | 180 ± 5 | 182 ± 10 | 183 ± 10 |
| Daily water consumption, ml | 16 ± 2 | 52 ± 2 | 19 ± 3* | 20 ± 5* | 25 ± 6* |
| Glucose, mmol/l | 4.2 ± 0.2 | 18.5 ± 1.0 | 6.3 ± 0.2* | 5.0 ± 0.2* | 5.5 ± 0.3* |

TABLE 6

| Values | Intact | Diabetes | Diabetes + metmorphin | Diabetes + MC-207 | Diabetes + MC-213 |
|---|---|---|---|---|---|
| In 10 days | | | | | |
| Cholesterol, mmol/l | 1.5 ± 0.3 | 7.0 ± 0.2 | 2.4 ± 0.3* | 2.5 ± 0.3* | 2.7 ± 0.5* |
| Total lipids, g/l | 10.1 ± 0.3 | 17.5 ± 1.2 | 10.5 ± 0.5 | 10.2 ± 0.5* | 10.5 ± 0.5* |
| Tri-glycerides, mmol/l | 2.5 ± 0.3 | 2.7 ± 0.3 | 2.6 ± 0.1* | 2.5 ± 0.2* | 2.5 ± 0.3 |
| β-lipoproteins, g/l | 1.9 ± 0.3 | 4.8 ± 0.2 | 2.2 ± 0.4* | 2.0 ± 0.2* | 2.2 ± 0.2* |
| Glycosylated hemoglobin, mol % | 5.0 ± 0.5 | 8.3 ± 0.2 | 5.0 ± 0.1* | 5.1 ± 0.3* | 6.4 ± 0.3* |
| In 20 days | | | | | |
| Cholesterol, mmol/l | 1.3 ± 0.2 | 8.0 ± 0.3 | 1.6 ± 0.3* | 1.5 ± 0.2* | 1.5 ± 0.2* |
| Total lipids, g/l | 10.1 ± 0.3 | 18.5 ± 1.3 | 11.5 ± 1.0 | 10.2 ± 0.3* | 10.4 ± 1.0* |
| Tri-glycerides, mmol/l | 2.5 ± 0.3 | 2.9 ± 0.4 | 1.6 ± 0.2 | 1.8 ± 0.2* | 1.7 ± 0.2 |
| β-lipoproteins, g/l | 2.0 ± 0.3 | 4.5 ± 0.2 | 2.2 ± 0.4* | 2.1 ± 0.2* | 2.1 ± 0.2* |
| Glycosylated hemoglobin, mol % | 5.0 ± 0.5 | 12.5 ± 0.3 | 6.1 ± 0.2* | 5.0 ± 0.3* | 6.2 ± 0.5* |

*significant difference from the non-treated animal group ($p < 0.05$).

The results show that all studied drugs exert marked therapeutic effect during moderate diabetes, and the efficiency of the drugs is comparable to, or in some cases even exceeds the efficiency of metmorphine at that. All animals treated by the drugs showed reduced blood glucose levels and normalized lipid metabolism values. This was also confirmed by histological examination of the pancreas.

EXAMPLE 3

Histological Examination of the Pancreas

Histological examination of pancreatic structure was carried out using the haematoxylin-eosin and aldehyde fuchsine staining of pancreatic sections using standard techniques. The photographs of stained pancreatic sections illustrating this example are presented in FIGS. 1-9.

EXAMPLE 4

Figure 1:
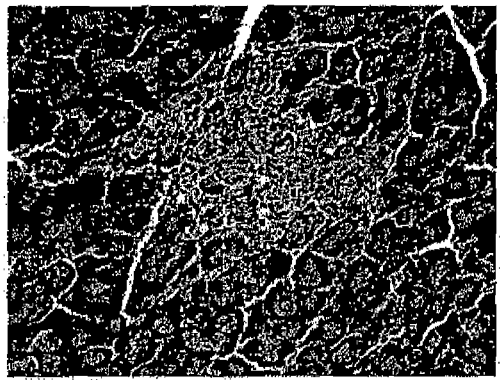
FIG. 1: Alloxan diabetes in rats, day 10. Deterioration of Langerhans islets structure. Haematoxylin-eosin staining, magnification 40×7.
Figure 2:
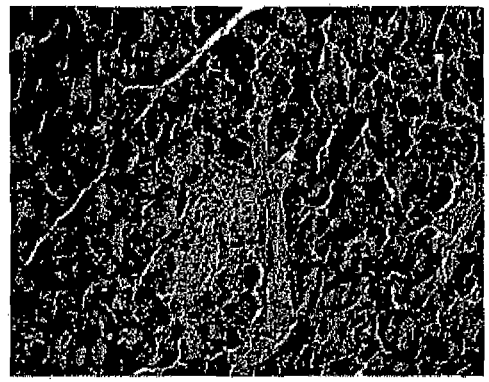
FIG. 2: Alloxan diabetes in rats, day 10. Destruction of the Langerhans islet. Cell lysis and reduction in the number of nuclei. Haematoxylin-eosin staining, magnification 40×7.
Figure 3:
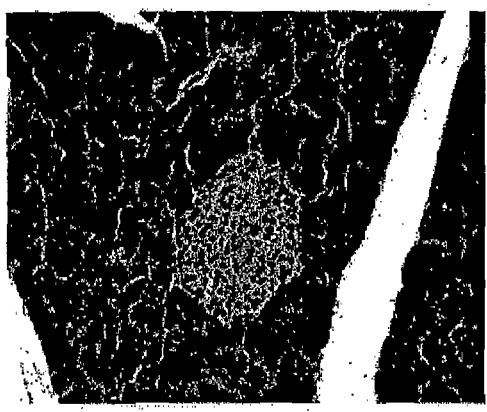
FIG. 3: Normal structure of Langerhans islet, day 10. Haematoxylin-eosin staining, magnification 40×7.
Figure 4:
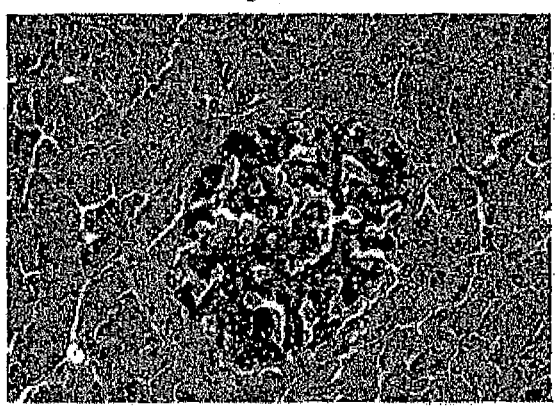
FIG. 4: Normal structure of pancreatic Langerhans islet of intact rat, day 20. Aldehyde fuchsine staining, magnification 20×7.
Figure 5:
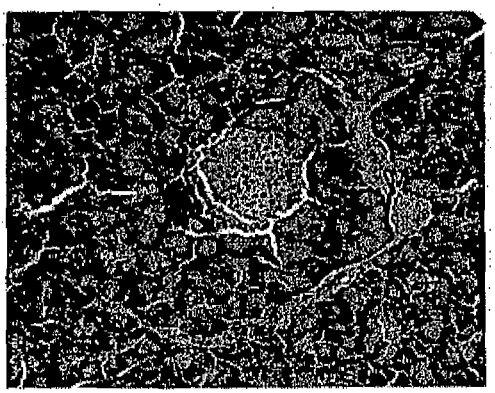
FIG. 5: Restoration of pancreatic Langerhans islet of experimental rat in 20 days after metmorphine treatment. Increased number of cells and nuclei. Haematoxylin-eosin staining, magnification 40×7.
Figure 6:
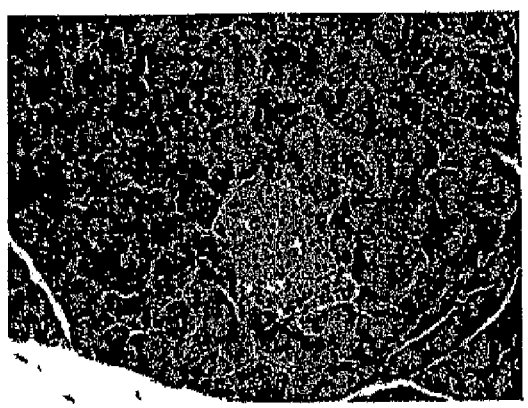
FIG. 6: Restoration of pancreatic Langerhans islet of experimental rat in 20 days after the MC-200 drug treatment. Increased number of cells and nuclei. Haematoxylin-eosin staining, magnification 40×7.
Figure 7:
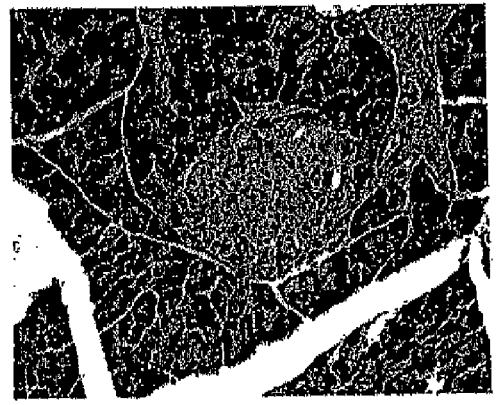
FIG. 7: Restoration of pancreatic Langerhans islet of experimental rat in 20 days after the MC-217 drug treatment. Increased number of cells and nuclei. Haematoxylin-eosin staining, magnification 40×7.
Figure 8:
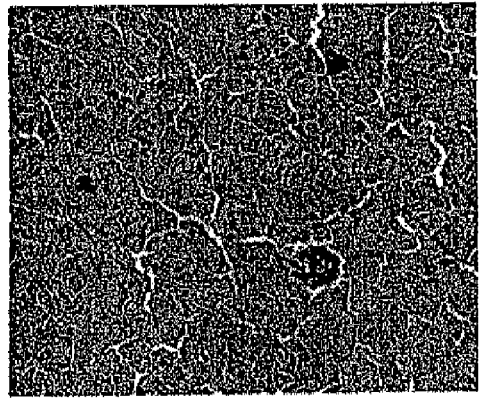
FIG. 8: Restoration of pancreatic Langerhans islet of experimental rat in 20 days after metmorphine treatment. Increased number of cells and nuclei. Aldehyde fuchsine staining, magnification 20×7.
Figure 9:
FIG. 9: Restoration of pancreatic Langerhans islet of experimental rat in 20 days after the MC-217 drug treatment. Marked increase of the islet size, the number of cells and insulin-synthesizing cell number. Aldehyde fuchsine staining, magnification 20×7.

Pharmaceutical Composition Production for Preparation of Tablet Mass

A mixture containing 0.5 kg of the MC-200 compound, 2.26 kg of potato starch, 5.5 g of polyvinyl pyrrolidone, 11.5 g of methylcellulose, 7 g of calcium stearate and 0.10 g of stearic acid is produced. The mixed mass is used for tablet preparation.

According to the invention, pharmaceutical compositions in the form of tablets, containing other compounds as an active ingredient, are produced in the same way.

EXAMPLE 5

Pharmaceutical Composition Production for Preparation of Capsules Containing 100 mg of Active Substance 100 g of the MC-217 compound, 28 g of potato starch, 59 g of microcrystalline cellulose, 2 g of silica dioxide, 9 g of collidone 25, and 2 g of calcium stearate are carefully mixed. The powder-like mixture is packed by 200 mg in gelatin capsules of suitable size.

EXAMPLE 6

Preparation of pharmaceutical composition for injections. 1 g of the MC-212 compound is mixed with 100 ml of ready-made 0.9% sodium chloride solution. The solution is filtered, and the made-up product is dispensed into ampoules and used for the intramuscular and intravenous injections.

The invention claimed is:

1. A method for the treatment of non-insulin-dependent diabetes, comprising administering to a patient having non-insulin-dependent diabetes a pharmaceutical composition comprising a therapeutically effective amount of a compound of general formula (I):

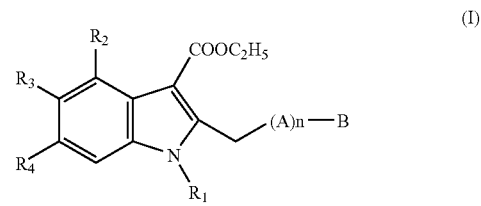

where:
$R_1$ is selected from the group consisting of an optionally substituted alkyl, an optionally substituted oxyalkyl, an optionally substituted cycloalkyl, an optionally substituted heterocyclil, and an optionally substituted aryl, wherein the optional substituent(s) may be one or more members selected from lower alkyl, halogen, oxyalkyl, hydroxyl, and amino;

$R_2$ is —H, or —CH$_2$NR'R"; where R' and R", independently of each other, are each selected from the group consisting of hydrogen, optionally substituted alkene, optionally substituted alkyl, optionally substituted cycloalkyl, optionally substituted alkoxy, optionally substituted heterocyclil, and optionally substituted aryl, or where R' and R", along with the nitrogen atom with which they are bound, form guanidyl or optionally substituted azaheterocyclil;

$R_3$ is an alkoxy group, or —OH;

or $R_2$ and $R_3$ form together an optionally substituted oxazine cycle;

$R_4$ is selected from the group consisting of hydrogen, halogen, cyano, NO$_2$, trifluoromethyl, optionally substituted aryl and optionally substituted heterocyclil;

A represents —S—, —SO—, —SO$_2$—, and n =0-1;

B represents —(CH$_2$)$_k$—R$_5$, where k =0-2, and where R$_5$ is an optionally substituted aryl, an optionally substituted alkyl, an optionally substituted oxyalkyl, or an optionally substituted heterocyclil, or where R$_5$ represents a substituent of the type:

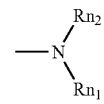

where Rn$_1$, and Rn$_2$ are defined according to the definitions of the substituents R' and R" above; or hydrates and/or pharmaceutically acceptable salts thereof.

2. A method according to claim 1, wherein the compound of formula (I) is the 1-methyl-2-phenylthiomethyl-3-carbethoxy-4-dimethylaminomethyl-5-hydroxy-6-bromoindole hydrochloride represented by the following formula :

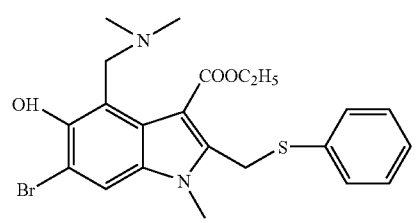

*HCl*H$_2$O .

3. A method according to claim 1, wherein the compound of formula (I) is the 1-methyl-2-pyrrolidinyl-1-methyl-3-carbethoxy-5-hydroxy-6-(pyridine-3-yl) indole represented by the following formula:

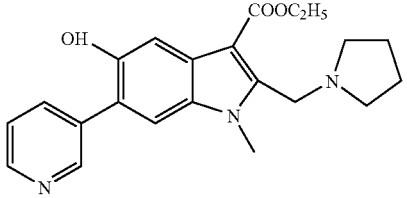

or pharmaceutically acceptable salts and/or hydrates thereof.

4. A method according to claim 1, wherein the compound of formula (I) is the 1-methyl-2-pyrrolidinomethyl-3-carbethoxy-4-dimethylaminomethyl-5-hydroxy-6-(pyridine-3-yl) indole represented by the following formula:

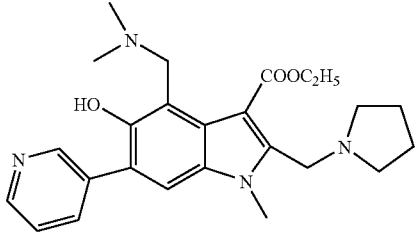

or pharmaceutically acceptable salts and/or hydrates thereof.

5. A method according to claim 1, wherein the compound of formula (I) is the 1-methyl-2-dimethylaminomethyl-3-carbethoxy-4-pyrrolidinomethyl-5-hydroxy-6 (pyridine-3-yl) indole represented by the following formula:

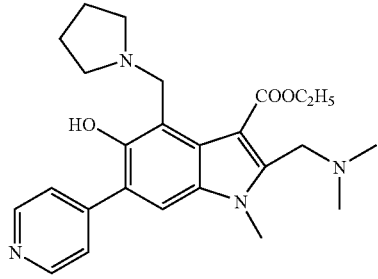

or pharmaceutically acceptable salts and/or hydrates thereof.

6. A method according to claim 1, wherein the compound of formula (I) is the methyl-2-B-naphthylthiomethyl-3-carbethoxy-4-dimethylaminomethyl-5-hydroxy-6-bromo indole represented by the following formula:

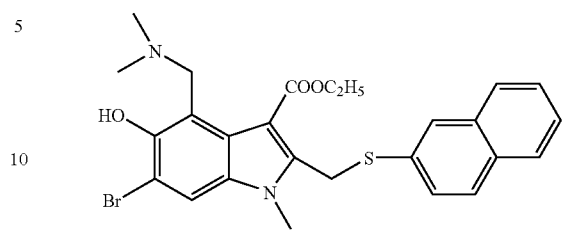

or pharmaceutically acceptable salts and/or hydrates thereof.

7. A method according to claim 1, wherein the compound of formula (I) is the 9-carbethoxy-2,7-dimethyl-5-pyridine-3-yl-8-[(pyrrolidin-1-yl)methyl]-1,2,3,7-tetrahydro [1,3] oxazino [5,6-e]indole represented by the following formula:

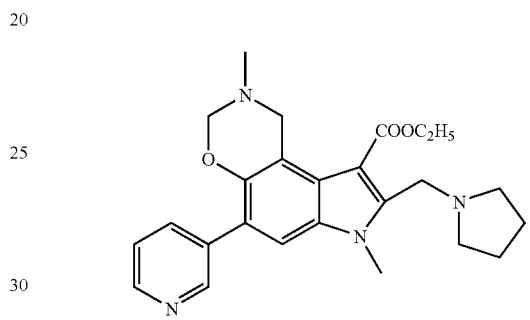

or pharmaceutically acceptable salts and/or hydrates thereof.

8. A method according to claim 1, wherein the compound of formula (I) is selected from the group consisting of:
1-methyl-2-phenylsulfonylmethyl-3-carbethoxy-4-dimethylamino methyl-5-hydroxy-6-bromoindole,
1-methyl-2-phenylsulfinylmethyl-3-carbethoxy-4-dimethylaminomethyl-5-hydroxy-6-bromoindole,
1-methyl-2-phenylsulfonylmethyl-3-carbethoxy-5-hydroxy-6-bromoindole,
1-methyl-2-phenylsulfinylmethyl-3-carbethoxy-5-hydroxy-6-bromoindole,
or pharmaceutically acceptable salts and/or hydrates thereof.

9. A method according to claim 1 wherein said pharmaceutical composition is administered in the form of tablets, granules, capsules, suspensions, solutions or injections.

10. A method according to claim 1 wherein said pharmaceutical composition includes one or more pharmaceutically acceptable carriers and/or excipients.

* * * * *